(12) United States Patent
Musi

(10) Patent No.: US 9,220,753 B1
(45) Date of Patent: Dec. 29, 2015

(54) PRODUCT FOR LOSING WEIGHT

(71) Applicant: Juan Carlos Musi, Miami, FL (US)

(72) Inventor: Juan Carlos Musi, Miami, FL (US)

( * ) Notice: Subject to any disclaimer, the term of this patent is extended or adjusted under 35 U.S.C. 154(b) by 0 days.

(21) Appl. No.: 14/749,259

(22) Filed: Jun. 24, 2015

(51) Int. Cl.
| | |
|---|---|
| *A61K 36/00* | (2006.01) |
| *A61K 36/45* | (2006.01) |
| *A61K 38/17* | (2006.01) |
| *A61K 31/555* | (2006.01) |
| *A61K 36/185* | (2006.01) |
| *A61K 36/77* | (2006.01) |
| *A61K 36/82* | (2006.01) |
| *A61K 36/11* | (2006.01) |
| *A61K 31/205* | (2006.01) |
| *A61K 38/16* | (2006.01) |

(52) U.S. Cl.
CPC ............ *A61K 38/1709* (2013.01); *A61K 31/205* (2013.01); *A61K 31/555* (2013.01); *A61K 36/11* (2013.01); *A61K 36/185* (2013.01); *A61K 36/45* (2013.01); *A61K 36/77* (2013.01); *A61K 36/82* (2013.01); *A61K 38/168* (2013.01)

(58) Field of Classification Search
None
See application file for complete search history.

*Primary Examiner* — Qiuwen Mi

(74) *Attorney, Agent, or Firm* — Jesus Sanchelima, Esq.; Christian Sanchelima, Esq.

(57) ABSTRACT

A composition to facilitate the elimination of water and dissolving fat in a user's body that includes chromium picolinate, protein, hibiscus flower (*Hibiscus sabdariffa*), horsetail (*Equisetum arvense*), guarana extract, green tea (*Camellia sinesis*), boldo leaf (*Peumus boldus*), cranberry extract, birch bark (*Betula alba*), and L-carnitine. The resulting powder product is mixed with water to achieve the targeted results. Optionally, a flavoring product component is added.

7 Claims, No Drawings

PRODUCT FOR LOSING WEIGHT

BACKGROUND OF THE INVENTION

1. Field of the Invention

The present invention relates to a product or composition for losing weight and, more particularly, to such a composition that is based on the elimination of body liquids, fat and toxins including sodium.

2. Description of the Related Art

Several products for reducing weight have been developed in the past. None of them, however, include a calibrated combination of protein and diuretic elements that facilitate the elimination of body liquids, toxins, sodium and dissolving accumulated fat.

SUMMARY OF THE INVENTION

It is one of the objects of the present invention to provide a product that facilitates the safe elimination of body liquids, toxins, sodium and dissolution of fat in a user's body.

It is another object of this invention to provide such a product that is stable and with long shelf life.

It is yet another object of this invention to provide such a product that is inexpensive to produce while retaining its effectiveness.

Further objects of the invention will be brought out in the following part of the specification, wherein detailed description is for the purpose of fully disclosing the invention without placing limitations thereon.

DETAILED DESCRIPTION OF THE EMBODIMENTS OF THE INVENTION

The present invention relates to a product that, in one of its embodiments, it includes by weight the following:

| | |
|---|---|
| a. chromium picolinate | 0.550 mg |
| b. whey protein | 11111.111 mg |
| c. hibiscus flower | 750.000 mg |
| d. guarana | 750.000 mg |
| e. cranberry (fruit) | 500.000 mg |
| f. horsetail (herb) | 30.000 mg |
| g. green tea (leaf) | 30.000 mg |
| h. boldo leaf (herb) | 20.000 mg |
| i. birch bark | 10.000 mg, and |
| j. L-carnitine | 206.186 mg |

The product components can be varied pursuant to the following ranges:

| | |
|---|---|
| a. chromium picolinate | 0.055 to 11.000 mg |
| b. whey protein | 1111.111 to 222,222.220 mg |
| c. hibiscus flower | 75.000 to15000.000 mg |
| d. guarana extract | 75.000 to15000.000 mg |
| e. cranberry (fruit) extract | 50.000 to10000.000 mg |
| f. horsetail (herb) | 3.000 to 600.000 mg |
| g. green tea (leaf) | 3.000 to 600.000 mg |
| h. boldo leaf (herb) | 2.000 to 400.000 mg |
| i. birch bark | 1.000 to 200.000 mg |
| j. L-carnitine | 20.619 to 4123.72 mg |

Protein, vegetable or animal, constitutes the bulk of the product. In one of the embodiments, whey protein is used. One of the whey proteins used is whey protein isolate such as the one produced by Agropur, MSI, LLC, La Crosse, Wis. See chart "1", attached.

One of the active ingredients in the composition subject of the present application is chromium picolinate. It is a chemical compound used as a nutritional supplement to prevent or treat chromium diseases. Chromium picolinate is a mineral that helps in weight loss, is helpful in developing muscle and burning fat simultaneously, breaks atoms and molecules from fat and are removed because they become soluble and additionally suppresses cravings. The chromium picolinate used in one of the embodiments is produced by Dongyu USI, Irvine, Calif. See chart "2", attached.

In addition to chromium picolinate, the present invention includes a natural diuretic component. This component includes a combination of naturally occurring substances found in herbs, such as: hibiscus flower (*Hibiscus sabdariffa*), horsetail (Equisetum *arvense*), green tea (*Camellia sinensis*), boldo leaf (*Peumus boldus*), and birch bark (*Betula alba*).

The hibiscus flower (*Hibiscus sabdariffa*) is used for food coloring and also as a condiment. *Hibiscus* flowers, in the present invention, are preferably in powder form. The hibiscus flower helps internal cleansing and eliminates excess water in the body. The hibiscus flower helps to decrease cholesterol and trygliceryds levels, improve digestion and muscle recovery. The hibiscus flower used is the one produced by Nutraceuticals International Group located in Bloomingdales, N.J. See attached chart "3".

Horsetail plant (*Equisetum arvense*) has been used in traditional medicine as tea, externally as baths or compressors, for treatment of disorders of fluid retention, the skin, locomotor system, kidneys and urinary tract, rheumatism and gout. One of the powders that can be used for the horsetail product is derived from fresh shoots and is produced by FCC Products, Inc., Livingston, N.J. See attached chart "4".

Green tea (*Camellia sinensis*) are the leaves and leaf bulb to produce tea. In the present invention, the green tea leaves are used in powder form, as an herbal derivative from green tea leaves. Some benefits of green tea are that it helps the body cleanse itself of accumulated toxins when expelling retained liquids, antioxidant, stimulates immunity and reduces anxiety. One of the green tea powders that can be used is produced by Harten Corporation. See chart "5", attached.

Boldo leaves (*Peumus boldus*) are used in powder form, in the present invention, as an herbal derivative. The boldo leaf is an excellent detoxifier, helps eliminate toxins and excess liquid retained in the body, facilitates fat burning and contributes to intestinal function. One of the boldo leaves powder that can be used is produced by Elements, LLC, Englewood, N.J. See attached chart "6".

Birch bark (*Betula alba*) powder is derived from the leaves and bark. Birch is known for its purifying and detoxifying effects, contributes naturally to weight loss, and favors the elimination of liquids from the body. One of the birch bark powders that can be used is produced by FCC Products, Inc. Livingston, N.J. See chart "7", attached.

Cranberry extract powder is derived from the fruit plant. Some benefits include contains high levels of antioxidants and helps prevent urinary infections. One of the cranberry powders that can be used is produced by BI Nutraceuticals, Long Beach, Calif. See chart "8", attached.

The guarana powder is derived from the fruit and it is a thermogenic product that helps increase the metabolism and burns calories. Guarana produces slow release energy, relieves fatigue, suppresses the appetite, and improves muscle recovery. One of the guarana products that can be used is produced by Naturex, Inc., South Hackensack, N.J. See chart "9".

L-carnitine is an amine quaternary, present in the diet and metabolized by the liver and the kidney from precursor amino acids (lysine, metionita). Elevated concentrations of L-carnitine in the cell improve lipid transport to mitochondria and so provide more substrates for the functioning of the metabolism of lipdos. An increase in the oxidation of fatty acids may increase the availability of CoA (Coenzyme A), improve the flow through the Krebs cycle and increase the activity of the enzyme pyruvate dehydrogenase, which, in turn, promotes the metabolism of glucose and can improve physical performance in high intensity exercise, which under normal conditions would be limited by the accumulation of lactate and hydrogen ions.

L-carnitine, when combined with chromium picolinate, results in a powerful effect to destroy and dissolve fat molecules. And the combination of the natural diuretic component, carries out and eliminates semi-dissolved fat through the urine. The combined composition also helps in the elimination of salts that retain liquids. All this with the aid of the guarana that produces an exothermic reaction. In this manner, a user burns more calories, carbohydrates, and fat because guarana has energy releasing caffeine. This product can be consumed before and after exercising and it is a unique product for losing weight allowing for the recuperation of muscles and simultaneously eliminating toxins.

The product, subject of the present application and one of its preferred embodiments, is produced by preparing it in a batch tank, in one of the embodiments, 11,111.111 mg. of whey protein described above and adding 0.550 mg. of picolinate, 750.000 mg of hibiscus flower powder, 750.000 mg of guarana powder, 500.000 mg cranberry (fruit) 30.000 mg horsetail (herb), 30.000 mg of green tea (leaf) powder, 20,000 mg of boldo leaf (herb) powder and 10.000 mg of birch bark. Optionally, a flavor (chocolate, strawberry, vanilla or other flavors) is added.

The product's different component products can be varied pursuant to the ranges provided above and still obtain good results. Mechanical mixing of the products for at least two minutes results in a substantially homogeneous mixture.

A user is directed to consume, daily, at least 15 g of the resulting product mixture for a sufficient number of days to experience the results, namely, losing body liquids, fat, toxins and sodium while simultaneously increasing his/her disposable energy.

Flavoring substances (such as chocolate, strawberry-kiwi, vanilla, and mixed berries) can be added to the resulting powdered product.

The foregoing description conveys the best understanding of the objectives and advantages of the present invention. Different embodiments may be made of the inventive concept of this invention. It is to be understood that all matter disclosed herein is to be interpreted merely as illustrative, and not in a limiting sense.

What is claimed is:

1. A composition to facilitate the elimination of water and dissolution of fat in a user's body, consisting essentially of:
   A) between 1111.111 to 222,222.220 mg of protein;
   B) between 75.000 to 15000.000 mg of hibiscus flower;
   C) between 75.000 to 15000.000 mg of guarana extract;
   D) between 50.000 to 10000.000 mg of cranberry extract;
   E) between 3.000 to 600.000 mg of horsetail;
   F) between 3.000 to 600.000 mg of green tea;
   G) between 2.000 to 400.000 mg of boldo leaf;
   H) between 1.000 to 200.000 mg of birch bark;
   I) between 0.055 to 11.000 mg of chromium picolinate; and
   J) between 20.619 to 4123.72 mg of L-carnitine.

2. The composition set forth in claim 1 wherein the protein is whey protein.

3. The composition set forth in claim 2 wherein the composition has the following formula:

| | |
|---|---|
| A) chromium picolinate | 0.550 mg |
| B) whey protein | 11111.111 mg |
| C) hibiscus flower | 750.000 mg |
| D) guarana extract | 750.000 mg |
| E) cranberry extract | 500.000 mg |
| F) horsetail | 30.000 mg |
| G) green tea | 30.000 mg |
| H) boldo leaf | 20.000 mg |
| I) birch bark | 10.000 mg, and |
| J) L-carnitine | 206.186 mg |

4. The composition set forth in claim 3 further including a flavor product.

5. The composition set forth in claim 1 wherein the protein is a vegetable protein.

6. The composition set forth in claim 5 wherein the composition has the following formula:

| | |
|---|---|
| A) chromium picolinate | 0.550 mg |
| B) vegetable protein | 11111.111 mg |
| C) hibiscus flower | 750.000 mg |
| D) guarana extract | 750.000 mg |
| E) cranberry extract | 500.000 mg |
| F) horsetail | 30.000 mg |
| G) green tea | 30.000 mg |
| H) boldo leaf | 20.000 mg |
| I) birch bark | 10.000 mg, and |
| J) L-carnitine | 206.186 mg |

7. The composition set forth in claim 6 further including a flavor product.

* * * * *